United States Patent [19]

Brown et al.

[11] Patent Number: 6,019,985

[45] Date of Patent: Feb. 1, 2000

[54] IMMUNOSTIMULATION METHODS FOR PROVIDING DISEASE PROTECTION IN POULTRY

[75] Inventors: Jenaay M. Brown, Tampa, Fla.; Larry R. McDougald, Watkinsville, Ga.

[73] Assignee: Munova Corporation, Tampa, Fla.

[21] Appl. No.: 09/032,141

[22] Filed: Feb. 27, 1998

[51] Int. Cl.$^7$ .................. A61K 39/002; A61K 39/00; A61K 39/12; A61K 39/02; A61K 39/385

[52] U.S. Cl. ...................... 424/265.1; 424/184.1; 424/246.1; 424/422; 424/245.1; 424/193.1; 424/267.1; 424/234.1; 424/204.1; 424/816; 424/826; 424/269.1; 435/252.1; 435/252.32

[58] Field of Search .................. 424/184.1, 246.1, 424/422, 245.1, 234.1, 193.1, 204.1, 265.1, 267.1, 269.1, 816, 826; 435/252.1, 252.32

[56] References Cited

U.S. PATENT DOCUMENTS

| | | |
|---|---|---|
| 4,663,306 | 5/1987 | Cantrell . |
| 5,372,810 | 12/1994 | Onishi et al. . |
| 5,540,924 | 7/1996 | Onishi et al. . |

OTHER PUBLICATIONS

Vanselow. Veterinary Bulletin 57/11:881–896, 1987.
Corrier et al, Poultry Science. PSA&SPSS. Abstracts 68/Suppl 1 p34, 1989.
Drews. Klin. Wochenschr. 62:254–64, 1984.
Toth et al Avian Diseases 31:861–867, 1987.
Chinnah et al. Vaccine. 10/8:551–557, 1992.
Palladino et al. Cellular Immunol. 38:350–364, 1978.
Donahoe et al. J. Natl Cancer Inst. 60/4:829–833, 1978.
McDougald, Poultry Digest 53/3:20–21, 1994.
Smith, Rod, "Embrex Receives Approval for First in ovo IBD Vaccine," FEEDSTUFFS, p. 6, Mar. 17, 1997.
Brochure of Embrex, Inc., "INOVOJECT, Egg Injection System, An Automated in ovo Vaccine Delivery System Providing Improved Bird Performance and Reduced Hatchery Operation Costs," 1992.
S.R. Coates, D.K. Buckner, and M.M. Jensen, "The Inhibitory Effect of Corynebacterium Parvum and Pasteurella Multocida Pretreatment on Staphylococcal Synovitis in Turkeys," Avian Diseases, vol. 21, No. 2, pp. 319–322, Dec. 1976.
"Enhancing Broiler Immune Response, Solvay Researchers are Using the Acemannan Molecule from Aloe Vera to Boost Immune Response of Broilers," Broiler Industry, Sep., 1992.
B.W. Calnek, H. John Barnes, Charles W. Beard, Larry R. McDougald, Y.M. Saif, "*Diseases of Poultry*," Tenth Edition, Chapter 34, pp. 865–868.
H.S. Lillehoj, E.B. Lindblad, and M. Nichols, "Adjuvanticity of Dimethyl Dioctadecyl Ammonium Bromide, Complete Freund's adjuvant and *Corynebacterium parvum* with Respect to Host Immune Response to Coccidial Antigens," Avian Diseases 37:731–740, 1993.
Andrea M. Miles, Vivian W. Doelling, Patricia V. Phelos, Catherine A. Flicks, Jullus K. Tyczkowski, Craig E. Whitfill and Richard P. Gildersleeve, "Efficacy of an Immunostimulant Administered in ovo Against Early Chick Mortality," Abstracts of Papers, No. 391, p. 131.

*Primary Examiner*—Nita Minnifield
*Attorney, Agent, or Firm*—Workman, Nydegger & Seeley

[57] ABSTRACT

Methods are provided for improved immunization against coccidiosis and other bacterial, viral, or parasitic diseases in poultry. One method includes administering a solution of *Propionibacterium acnes* suspended in normal saline to a chick at age day one, following hatching. An anticoccidial vaccine and/or other vaccine is then administered to the chick such as by oral administration. Alternatively the method includes the steps of aseptically injecting *Propionibacterium acnes* in ovo at about day 18 in development, followed by post-hatching vaccination with an anticoccidial vaccine and/or other vaccine. Alternatively, either method can be utilized without the subsequent vaccination step for stimulating non-specific cell-mediated immune responses in poultry.

52 Claims, No Drawings

IMMUNOSTIMULATION METHODS FOR PROVIDING DISEASE PROTECTION IN POULTRY

BACKGROUND OF THE INVENTION

1. The Field of the Invention

The present invention is directed generally to methods and apparatus for preventing diseases in poultry. More specifically the present invention is related to methods and apparatus for immunizing poultry against diseases caused by bacteria, viruses, and parasites.

2. The Relevant Technology

Commercial poultry husbandry and breeding practices have resulted in immune system deficiencies in chickens making disease more prevalent and devastating to the birds.

Coccidiosis is a disease which costs the poultry industry hundreds of millions of dollars annually. This disease is primarily caused by parasites from the genus Eimeria. These parasites have short, direct life cycles and high reproductive potentials which intensifies the potential for outbreaks of disease, especially where 15–30,000 chickens are housed in total confinement. McDougald, L. R., Reid, W. M., *Coccidiosis*, Diseases of Poultry, (B. W. Calnek et al. eds., 1 0th ed. 1997).

Eimeria parasites multiply in the intestinal tract where they cause tissue damage. This further results in the interruption of feeding and digestive processes or nutrient absorption; dehydration; blood loss; and increased susceptibility to other disease agents. Further, immunosuppressive diseases may act in concert with coccidiosis to produce a more severe disease. Id.

Coccidia are almost universally found wherever chickens are raised, and especially in broiler farms where the chickens are kept for only about 6–8 weeks prior to market. The ubiquitous nature of coccidia in poultry precludes the possibility of elimination or prevention of coccidia by quarantine, disinfection, and sanitation. Id.

Coccidial infections depend largely on the number of parasite oocysts ingested and on the immune status of the bird. Characteristics useful in identification of the species of parasite include location of the lesions in the intestine; appearance of the gross lesion; oocyst size, shape and color; location of parasites in tissues; etc. Id.

Prevention of this disease has been attempted by supplying young poultry with continuous medication of anticoccidial drugs. Vaccines against coccidiosis have met with limited success and have been used mostly in breeders and in turkeys. Conventionally, vaccination of broilers was rare due to the risk associated with the birds contracting a light infection from the vaccine, which could affect weight gain, feed conversion, and skin pigmentation. Id.

SUMMARY AND OBJECTS OF THE INVENTION

It is a primary object of the present invention to provide an immunostimulant for stimulating non-specific cell mediated immunity against diseases in poultry caused by viruses, bacteria, or parasites with the benefits of early immunization.

Another object of the present invention is to utilize *Propionibacterium acnes* as an immunostimulant for delivery to poultry at one day of age.

It is another object of the present invention to utilize *Propionibacterium acnes* as an immunostimulant for delivery to poultry in ovo.

Yet another object of the present invention is to utilize *Propionibacterium acnes* as an immunostimulant for providing protection against diseases in poultry without the need for additional immunization steps or vaccines.

It is still another object of the present invention to provide an improved method for immunizing broiler chickens against coccidiosis.

These and other objects and features of the present invention will become more fully apparent from the following description and appended claims, or may be learned by the practice of the invention as set forth hereinafter.

To achieve the forgoing objects, and in accordance with the invention as embodied and broadly described herein, the present invention relates to new and useful methods for inoculating poultry, especially broiler chickens, against coccidiosis. One preferred method administers *P. acnes* in saline to chicks intraperitoneally at about one day of age. Another preferred method inoculates chicks in ovo at about day 18 with a preparation of *Propionibacterium acnes* in saline.

In an alternate embodiment, the chicks are further vaccinated with an anticoccidial vaccine. Alternatively, vaccines for bacterial, viral, or other parasitic diseases are utilized in place of or in conjunction with the anticoccidial vaccine.

DETAILED DESCRIPTION OF THE PREFERRED EMBODIMENTS

Immunization is the process by which an immune response is induced for protection against certain diseases. An immune response is either "humoral" or "cell-mediated." A humoral response is initiated when a foreign protein, or, "antigen," activates the production of antibodies designed to specifically attach to the foreign protein that induced them. Cell-mediated immune responses involve the production of specialized cells that react with antigens on the surface of host cells, either killing the host cell or inducing other cells (macrophages) to destroy the antigen. Unlike the humoral antibody response, cell-mediated responses are not specific to the antigen that induced them.

Commercial poultry husbandry has resulted in immune system deficiencies in poultry, making them more susceptible to disease. Various immunization techniques have been developed in an attempt to counteract the effects of the reduced immunity.

One of the main types of immunization involves the use of vaccines, which are utilized for specific (humoral) stimulation of the immune system. In a vaccination, killed or weakened pathogenic microorganisms are introduced into the body to sensitize the immune system to those pathogens. If disease-causing organisms of the same type later enter the body, the immune system should quickly destroy them.

Certain vaccines have been developed for administration in ovo. It is believed vaccination prior to hatching of the chick reduces the amount of post-hatch chick handling and eliminates the stress of individually injecting the newly hatched chicks, which leads to improved chick performance. Further, it is believed that when the embryo is vaccinated in ovo, disease resistance builds during the last days of incubation and provides the hatched chicks with ahead start on resisting disease. A system known as INOVOJECT® manufactured by Embrex, Inc., injects biologically active compounds in ovo, directly into the egg, just 3 days before the chick is hatched. When the chick hatches, it is already vaccinated and ready for transport to a growout farm. Embrex, Inc., *Inovoject® Egg Injection System Product Literature* (1992).

Further, in ovo inoculation on day 18 of incubation with a material (an immunostimulant inducing lymphokines)

which non-specifically stimulates the immune system was found to decrease early chick mortality by 30 to 50% below the controls in numerous trials involving eggs from commercial broiler breeder flocks. It was suggested that this protocol would have practical application in stimulating the resistance of broiler chicks to early mortality associated with *E-coli* organisms. Andrea M. Miles, et al., *Abstract: Efficacy of an Immunostimulant Administered in Ovo Against Early Chick Mortality* (1993).

A vaccine against Infectious Bursal Disease has also been developed for delivery in ovo. However, it is currently believed that other vaccines are risky and unsafe when delivered into the embryo, causing the chicks to be born sick or stillborn. Rod Smith, *Embrex Receives Approval of First in Ovo IBD Vaccine*, Feedstuffs at 6 (Mar. 17, 1997).

Coccidiosis is a serious parasitic disease in poultry. Vaccines against this disease have met with limited success. In broiler chickens, for example, vaccination may result in the appearance of a light infection which can detrimentally affect the commercial characteristics of the birds.

The present invention is directed to an improved method for inoculating chicks at an early developmental stage against coccidiosis-type diseases. Specifically, the present invention is directed to the use of *Propionibacterium acnes* for stimulating non-specific cell mediated immune responses in poultry at an age as early as day one, or even in ovo, to combat coccidiosis and other poultry diseases.

Poultry as the term is used herein refers to one or a plurality of game or domesticated birds for use as food, such as chickens, turkeys, quail, pheasants, ratites (flightless birds), etc. The methods of the present invention are also useful for preventing disease in exotic and domesticated pet birds; thus the general term poultry is meant to encompass those birds as well.

Further, as the term is used herein, "chick" is meant to refer to young birds in ovo or post-hatching, and up to about four to six weeks of age. The term in ovo refers to the embryonic developmental stage of the chick prior to hatching. In addition, as the term is used herein, chick refers to any type of poultry, although it will be appreciated that broiler chickens are the preferred poultry recipients for the methods of the present invention. Thus, for the purposes of the present invention, the developmental stages and characteristics described herein are directed to broiler chickens. One of skill in the art could easily determine the appropriate corresponding developmental stage for other types of poultry.

The standard incubation time for an embryonic chick is twenty-one days. Thus, a chick is typically in ovo for about twenty-one days prior to hatching. After hatching, the chick is referred to as being a certain age old, i.e., the chick is one day old, or three weeks old. The day that the chick hatches is considered to be day zero for the purposes of this invention.

The components necessary to effectuate the methods of the present invention comprise the microorganism, *Propionibacterium acnes*, and a diluent in which the *Propionibacterium acnes* is suspended.

*Propionibacterium acnes*, hereinafter, "*P. acnes*," is an immunostimulant for providing non-specific cell-mediated immune response in poultry. *P. acnes* is available in a variety of forms including freeze-dried (lyophilized), liquid suspension, or dried powder. A dried powder form of *P. acnes* is the presently preferred embodiment for the method of the present invention.

The *P. acnes* is preferably suspended in a diluent. A preferred diluent for suspending the *P. acnes*. is normal, also referred to as "physiological," saline solution. Alternatively, an amino acid diluent is utilized in accordance with the present invention. It should be appreciated that other diluents capable of suspending the *P. acnes* for administration into chicks could be utilized in accordance with the present invention.

Alternatively, a variety of materials can be added to a diluent in accordance with the present invention depending on the requirements of the chicks. For example antibiotics (gentamicin, ceftiofur, and erythromycin), vaccines (Marek's Disease vaccine, Infectious Bursal Disease vaccine), vitamins, growth media (tryptose phosphate), meat digests, and/or food colorings may be added to a diluent in accordance with the present invention.

The *P. acnes* is preferably suspended in a normal saline diluent at about 0.5 mg to about 10 mg dried weight per milliliter of diluent. It will be appreciated that other initial concentrations of the *P. acnes* suspension are within the scope of the present invention because the actual administration to the chick is preferably adjusted and further diluted with diluent for optimum dosages. The optimum dosage for administration of the *P. acnes* suspension depends upon the different modes of administration, which will be described in more detail hereinbelow, and also on the amount of *P. acnes* suspension, hereinafter the "effective amount," which results in stimulation of the immune system such that the effects of coccidiosis, including deaths, intestinal lesions, and weight loss, are reduced.

For example, in one preferred mode of administration, the *P. acnes* suspension is administered to the chick at a concentration of about 20 $\mu$g/mL. Those of skill in the art will appreciate that the starting concentration of the *P. acnes* suspension is simply diluted with the same diluent in which the *P. acnes* was originally suspended until a desired final dose is realized.

In a preferred method of the present invention, an effective amount of *P. acnes* suspension such as that described herein above is administered to hatched chicks. The preferred age for hatched chicks ranges from immediately post-hatching to about one week old. A more preferred age for hatched chicks ranges from about day zero to about three days old. The most preferred age for hatched chicks is about one day old.

A preferred dose in accordance with the method of the present invention is about 0.1 mL of *P. acnes* suspension at a range from about 0.5 $\mu$g/chick to about 16 $\mu$g/chick. A more preferred dose in accordance with the method of the present invention is about 0.1 mL of *P. acnes* suspension at a range from about 1.5 $\mu$g/chick to about 3.5 $\mu$g/chick. A most preferred dose in accordance with the method of the present invention is about 0.1 mL of *P. acnes* suspension at a dose of about 2 $\mu$g/chick.

The preferred mode of administration of the *P. acnes* suspension for hatched chicks is via intraperitoneal injection. Alternatively, the *P. acnes* suspension is administered to hatched chicks via subcutaneous injection in a method substantially similar to that described hereinabove.

In an alternate embodiment of the present invention, the method described above includes an additional vaccination step. For example, the hatched chicks are preferably vaccinated against coccidiosis via oral administration of an anti-coccidial vaccine. One example of such a vaccine is IMMU-COX® anticoccidial vaccine available from Vetech Laboratories. Alternatively, COCCIVAC® anticoccidial vaccine by Schering-Plough, or other commercial or autogenous vaccine is utilized. Alternatively, coccidial antigen may be utilized. It will also be appreciated that vaccines against other poultry diseases may be utilized in accordance with the method of the present invention. Any of the aforementioned vaccines can be provided to the chick in ovo or post hatch.

In one preferred embodiment of the present invention, the vaccination step is performed following administration of the P. acnes suspension. For example, the vaccination is administered via the food supply to the chicks at the age of about day three and beyond. Alternatively, the vaccine is incorporated into the food supply from day zero. Alternatively, the vaccine is administered simultaneously with the P. acnes suspension.

In an alternate embodiment of the method of the present invention, P. acnes is suspended in a diluent solution such as described hereinabove and administered to hatched chicks via an eye spray. The eye spray administration method does not cause the pain and stress to older chicks associated with conventional inoculation techniques. As the term is used herein, eye spray is synonymous with "in-house" spray, which is known by those of skill in the art to be used with older chicks.

The preferred time period during which eye spray is administered to chicks ranges from immediately after hatching to about four weeks or older. A more preferred time period ranges from about one day to about three weeks old.

A preferred dose for eye spray administration is P. acnes suspension at a range from about 2 μg/chick to about 16 μg/chick. A more preferred dose for eye spray administration is P. acnes suspension at a range from about 6 μg/chick to about 10 μg/chick. A most preferred dose for eye spray administration is P. acnes suspension at dose of about 8 μg/chick.

In an alternate embodiment of the eye spray administration method described above, an added step of vaccinating the chick with an anticoccidial vaccine and/or a vaccines against other diseases of poultry is performed.

In one embodiment, vaccination is performed at approximately the same time as the eye spray administration of the P. acnes solution. Alternatively, the vaccination is performed through oral administration following hatching of the chicks such at day zero, day one, and/or beyond.

In another alternate embodiment of the method of the present invention, P. acnes is administered to the chick in ovo during the embryonic development period. Prior to the present invention, it was believed that in ovo inoculation against coccidiosis would be detrimental to the chicks. The results of in ovo administration of P. acnes, however, illustrate that this is an effective method to stimulate non-specific cell-mediated immune response and prevent coccidiosis disease in chicks. See, e.g., Example 16, below.

To perform the in ovo method of the present invention, P. acnes is preferably suspended in a diluent solution such as described hereinabove. A preferred diluent solution is physiological saline.

An effective amount of the P. acnes suspension is then administered to chicks in ovo. The preferred developmental stage for administration to chicks in ovo ranges from about day 14 to immediately prior to hatching at about day 21. A more preferred developmental stage ranges from about day 17 to about day 19. The most preferred developmental stage for administration in ovo is at about day 18.

A preferred dose for in ovo administration is about 0.1 mL of P. acnes suspension at a range from about 2 μg/egg to about 12 μg/egg. A more preferred dose for in ovo administration is about 0.1 mL of P. acnes suspension at a range from about 6 μg/egg to about 10 μg/egg. A most preferred dose for in ovo administration is about 0.1 mL of P. acnes suspension at dose of about 8 μg/egg.

The P. acnes suspension is preferably injected through the large end of the egg at about one inch into the chorioallantoic membrane. Injection in ovo is preferably carried out under aseptic conditions.

In an alternate embodiment of the in ovo administration method described above, an added step of vaccinating the chick with an anticoccidial vaccine and/or vaccines against other diseases of poultry is performed.

In one embodiment, vaccination is performed simultaneously with the in ovo administration of the P. acnes solution. Alternatively, the vaccination is performed through oral administration following hatching of the chicks such at day zero, day one, and/or beyond.

With the exception of Example 1, the examples which follow are included to illustrate the effectiveness of P. acnes in preventing coccidiosis. The examples are meant to be illustrative only, and are not meant to limit the embodiments of the present invention.

With respect to the results of the studies depicted in the following examples, care should be taken to avoid drawing any conclusions based on the number of deaths, intestinal lesions, or on the weight gain alone. These factors should to be taken into account as a whole in determining the effectiveness of the various study parameters.

In Example 1, immunostimulants were utilized in conjunction with an anticoccidial vaccine in an attempt to ameliorate the difficulties associated with conventional vaccination against coccidiosis.

EXAMPLE 1 (Prior Art)

Three week old chickens were immunized intramuscularly with a mixture of anticoccidial vaccine and an immunostimulant of either *Propionibacterium acnes* (previously known as *Corynebacterium parvum*), or Complete Freund's adjuvant (CFA). The chickens were challenged ten days after immunization with the coccidial parasite, *Eimeria tenella*. Oocyst production was determined by collecting fecal samples 5–9 days following the coccidial challenge. The results of the study indicated that chickens immunized with CFA and anticoccidial vaccine showed significantly lower oocyst production than the controls immunized with CFA alone. However, when compared with the controls immunized with CFA alone, the P. acnes did not differ with respect to development of protective immunity. Lillehoj, H. S., Linblad, E. B., Nichols, M., *Adjuvanticity of Dimethyl Dioctadecyl Ammonium Bromide, Complete Freund's Adjuvant and Corynebacterium parvum with Respect to Host Immune Response to Coccidial Antigens,* 37 Avian Diseases 731 (1993).

In accordance with the investigations associated with the present invention, it is believed that vaccination at such as that described in Example 1 (three weeks or older) is unacceptable. Vaccination at this stage in development requires the difficult, painful, and impractical collection and inoculation of substantially grown chicks.

Additionally, the intramuscular administration associated with the method in Example 1 makes it difficult for the P. acnes to reach the immune system cells, macrophages, whose function it is to protect the body against infection.

For Examples 2 through 4, the following materials and methods were utilized and substantially duplicated for each example:

Materials and Methods

Mixed sex, day-old domestic broiler chicks (Gallus domesticus), were obtained from a research flock (Peterson males and Arbor Acres females). The chicks were randomly assigned, using a statistical analysis system (SAS) randomization program, to different treatment groups, depending upon the investigation performed. The *P. acnes* was reconstituted and diluted with physiological saline. The *P. acnes* was kept in solution by 12 occasional agitation of the container. The groups that did not receive *P. acnes* were treated in the same manner with physiological saline (sham inoculated). After hatching, the chicks were moved to an environmentally controlled building where they were housed separately by treatment group in 4'×10' plastic mesh floor pens, and placed on fresh litter. Incandescent lamps were used for additional brooding heat. A standard broiler starter ration and water were available ad libitum.

On about day 12, healthy chicks were selected from each treatment group, wing banded with individual numbers, weighed and moved to 6 Petersime battery cages (27"×27"×12"), housing 10 birds each. The excess birds were euthanized and incinerated.

Six days later, all birds were weighed, their body weights were recorded, and they were euthanized by cervical dislocation. Necropsies were then conducted on all birds and intestinal lesions were scored according to the Johnson and Reid scoring system. All remains were incinerated.

Experimental Data

Intestinal lesions, deaths, and weight gain were used for comparative analysis to determine the effectiveness of the *P. acnes* against coccidial infection. Intestinal lesions are indicative of different Eimeria species depending upon the location of the lesions in the intestine. Upper intestinal lesions indicate *E. acervulina* infection; middle intestinal lesions indicate *E. maxima* infection; cecal lesions indicate *E. tenella* infection.

Bodyweight gains are useful in determining coccidial infections because low weight is an indication of poor absorption of nutrients which is a primary symptom of a coccidial infection. These factors are analyzed as a whole for determination of the effectiveness of the *P. acnes* against coccidiosis.

General Linear Models (GLM) procedure for ANOVA and Duncan's Multiple Range Test was used for comparisons between treatment groups. Different superscript letters within a column in one of the following tables indicate a significant difference ($p \leq 0.05$).

EXAMPLE 2

On day one, 100 chicks (group one) were injected intraperitoneally with *P. acnes* at a dose of 4.0 µg/chick with an injection volume of 0.1 mL, and 200 chicks (groups two and three) received sham inoculation of physiological saline. None of the chicks received anticoccidial vaccine or any other drugs or vaccines during the study.

On about day 12, 60 chicks from group one and 60 chicks from group two were challenged with Eimeria species as follows: 50,000 *E. tenella* and 500,000 *E. acervulina* live oocysts by oral gavage.

The results of this study are depicted in Tables 1–3.

TABLE 1

| Group | P. acnes | Challenge | Upper Score | Cecal Score |
|---|---|---|---|---|
| 1 | 4.0 µg | Yes | 3.1[a] | 3.2[a] |
| 2 | 0.0 µg | Yes | 3.2[a] | 3.0[a,b] |
| 3 | 0.0 µg | No | 0.0[c] | 0.0[d] |

Table 2, below, depicts the number of coccidiosis-related deaths per treatment group six days following the coccidial challenge.

TABLE 2

| Group | Treatment Protocol | Coccidiosis Deaths |
|---|---|---|
| 1 | 4.0 µg P. acnes, challenged | 2 |
| 2 | 0.0 µg P. acnes, challenged | 4 |
| 3 | 0.0 µg P. acnes, not challenged | 0 |

Body weights were measured at six days post challenge and the weight gains were calculated. The mean weight gains are illustrated in Table 3, below.

TABLE 3

| Group | P. acnes (µg) | Challenge | Gains (grams) |
|---|---|---|---|
| 1 | 4.0 | Yes | 194.2[c] |
| 2 | 0.0 | Yes | 169.2[d] |
| 3 | 0.0 | No | 278.8[a] |

Discussion and Conclusions

When the results are viewed as a whole, a dose of 4.0 µg of *P. acnes* given intraperitoneally to day-old broiler chickens enhanced their immune response and decreased the negative effects of coccidiosis.

EXAMPLE 3

The procedure from Example 2 was followed with the added step that groups one and two received IMMUCOX® anticoccidial vaccine orally via gel pads in their pens. The results follow in Tables 4–6.

TABLE 4

| Group | P. acnes | Vaccine | Challenge | Upper Score | Cecal Score |
|---|---|---|---|---|---|
| 1 | 4.0 µg | Yes | Yes | 2.8[b] | 2.1[c] |
| 2 | 0.0 µg | Yes | Yes | 2.8[b] | 2.8[b] |
| 3 | 0.0 µg | No | No | 0.0[c] | 0.0[d] |

Table 5 depicts the number of coccidiosis-related deaths per treatment group six days following the coccidial challenge.

TABLE 5

| Group | Treatment | Coccidiosis Deaths |
|---|---|---|
| 1 | 4.0 µg P. acnes, vaccinated, challenged | 0 |
| 2 | 0.0 µg P. acnes, vaccinated, challenged | 2 |
| 3 | 0.0 µg P. acnes, not vaccinated, not challenged | 0 |

Body weights were measured at six days post challenge and the weight gains were calculated. The mean weight gains are illustrated in Table 6.

TABLE 6

| Group | P. acnes (μg) | Cocci. Vaccine | Challenge | Gains (grams) |
|---|---|---|---|---|
| 1 | 4.0 | Yes | Yes | 227.8[b] |
| 2 | 0.0 | Yes | Yes | 212.5[b,c] |
| 3 | 0.0 | No | No | 278.8[a] |

Discussion and Conclusions

A dose of 4.0 μg of P. acres given intraperitoneally to day-old broiler chickens enhanced their immune response and decreased the negative effects of coccidiosis when given in combination with an anticoccidial vaccine. Combining P. acnes and the anticoccidial vaccine reduced to zero the number of coccidiosis related deaths. Further, there was no mortality from other causes in birds receiving both the P. acnes and the anticoccidial vaccine.

EXAMPLE 4

Example 2, above, was substantially repeated in order to determine an optimum dosage or range thereof of P. acnes for intraperitoneal injection. The treatment groups were as follows in Table 7:

TABLE 7

| Group | P. acnes dose per chick | Anticoccidial Vaccine | Coccidiosis Challenge | Number of Chicks |
|---|---|---|---|---|
| 1 | 0 | No | No | 75 |
| 2 | 0 | No | Yes | 75 |
| 3 | 0 | Yes | No | 75 |
| 4 | 0 | Yes | Yes | 75 |
| 5 | 2.0 μg | Yes | Yes | 75 |
| 6 | 4.0 μg | Yes | Yes | 75 |
| 7 | 8.0 μg | Yes | Yes | 75 |
| 8 | 16.0 μg | Yes | Yes | 75 |

Discussion and Conclusions

The results of this study indicated that P. acnes given intraperitoneally to day-old broiler chickens gave better protection against the effects of coccidiosis than the oral anticoccidial vaccine given alone. Chicks that received 2.0 μg of P. acnes, in addition to an oral anticoccidial vaccine, had lower intestinal lesion scores in all areas than those given the vaccine alone. Those that received 4.0 μg of P. acnes, in addition to the vaccine, had the lowest lesion scores in all categories compared to any of the challenged groups.

Further, 4.0 μg of P. acres was significantly better than other levels of P. acnes, or vaccine alone, in decreasing the intestinal lesions associated with coccidiosis, and the dose level of 2.0 μg of P. acnes gave better weight gains and fewer deaths in addition to lowering the lesion scores. This suggests that a range from about 2.0 to about 4.0 μg is the optimum dose level for intraperitoneal administration to day-old broiler chicks for immune stimulation against the effects of coccidiosis.

EXAMPLES 5–15

Examples 1 and 2 are substantially repeated with the modifications in Table 8:

TABLE 8

| Example | Mode of Administration of P. acnes | Approx. Age |
|---|---|---|
| 5 | intraperitoneal injection | day zero |
| 6 | subcutaneous injection | day zero |
| 7 | eye spray | day zero |
| 8 | intraperitoneal injection | day three |
| 9 | subcutaneous injection | day three |
| 10 | eye spray | day three |
| 11 | intraperitoneal injection | day seven |
| 12 | subcutaneous injection | day seven |
| 13 | eye spray | day seven |
| 14 | eye spray | three weeks |
| 15 | eye spray | four weeks |

Discussion and Conclusions

P. acnes stimulates non-specific cell mediated immune response in chicks and effectively decreases the symptoms associated with coccidiosis via intraperitoneal, subcutaneous, or eye spray administration to chicks varying in age from day zero to four weeks old.

EXAMPLE 16

Domestic broiler (Gallus domesticus) embryos (fertile eggs), obtained from a research flock (Peterson males and Arbor Acres females), were placed in NATUREFORM® incubators in a poultry research facility. Temperature and humidity were maintained at 99.7° F. and 52% humidity. On day 18 of incubation, at transfer from setting to hatching incubators, the eggs were randomly assigned, using a SAS randomization program, to treatment groups as follows:

TABLE 9

| Group | P acnes dose per egg | IMMUCOX ® | Coccidiosis Challenge | Number of Embryos | Number of Chicks |
|---|---|---|---|---|---|
| 1 | 0 | No | No | 100 | 60 |
| 2 | 0 | No | Yes | 100 | 60 |
| 3 | 0 | Yes | No | 100 | 60 |
| 4 | 0 | Yes | Yes | 100 | 60 |
| 5 | 4 μg | Yes | Yes | 100 | 60 |
| 6 | 8 μg | Yes | Yes | 100 | 60 |
| 7 | 16 μg | Yes | Yes | 100 | 60 |

The P. acnes was reconstituted and diluted with physiological saline. Those groups selected to receive P. acnes treatment were then inoculated using aseptic technique through the large end of the egg at a depth of 1" into the chorioallantoic membrane, with their specific dose of P. acnes. The injection volume was 0.1 mL. Groups 2, 3 and 4 did not receive P. acnes but were injected in the same manner with physiological saline (sham inoculated). The eggs were then placed, by treatment group, into the baskets of a NATUREFORM® hatching incubator and incubated under 99.7° F. and 52% humidity until day 21 when all hatched chicks were removed, by group, to continue the study.

At one day of age chicks were moved to an environmentally controlled building. Here they were housed separately by treatment group in 4'×10' plastic mesh floor pens and placed on fresh litter. Incandescent lamps were used for additional brooding heat. A standard broiler starter ration and water was available ad libitum. IMMUCOX® anticoccidial vaccine available from Vetech Laboratories was administered via the oral route, in IMMUNOGEL® gel pad suspension available from Wingo, Inc., to groups 2, 4, 5, 6 and 7 on day one. No other drugs or vaccines were administered during the study.

At approximately 12 days of age, healthy chicks from each treatment group were selected, wing banded with individual numbers, weighed and moved to 6 Petersime battery cages (27"×27"×12"), housing 10 birds each. Birds in groups 2, 4, 5, 6 and 7 were challenged with Eimeria species as follows: 50,000 *E. tenella*, and 100,000 *E. maxima* (contaminated by approximately 50,000 *E. acervulina*) live oocysts by oral gavage. The excess birds were euthanized and incinerated.

Six days post challenge, all birds were weighed, and euthanized by cervical dislocation. Necropsies were then conducted on all birds and intestinal lesions were scored according to the Johnson and Reid scoring system. All remains were incinerated.

Upper intestinal lesions indicating *E. acervulina* infection, middle intestinal lesions indicating *E. maxima* infection, and cecal lesions indicating *E. tenella* infection, are presented in Table 10, below. General Linear Models (GLM) procedure for ANOVA and Duncan's Multiple Range Test was used for comparisons between treatment groups. Different superscript letters within a column indicate a significant difference ($p \leq 0.05$).

Body weights were measured six days post challenge and the weight gains from day of challenge were calculated. The mean body weight gains are listed in Table 12.

TABLE 12

| Group | P. acnes Dosage | IMMUCOX ® Vaccine | Coccidial Challenge | Mean Weight Gains (grams) |
|---|---|---|---|---|
| 1 | 0.0 | No | No | 267.5$^a$ |
| 2 | 0.0 | No | Yes | 164.0$^d$ |
| 3 | 0.0 | Yes | No | 218,6$^b$ |
| 4 | 0.0 | Yes | Yes | 199.0$^c$ |
| 5 | 4.0 μg | Yes | Yes | 206.0$^b$ |
| 6 | 8.0 μg | Yes | Yes | 160.8$^d$ |
| 7 | 16.0 μg | Yes | Yes | 189.0$^c$ |

Discussion and Conclusions

This study indicated that *P. acnes* is capable of stimulating non-specific cell-mediated immunity against a parasite in chickens when delivered via in ovo administration. Dose levels of 4.0 and 8.0 μg of *P. acnes* per embryo at day 18 of incubation followed by an anticoccidial vaccine at one day of age were effective in controlling coccidiosis infections, and were more effective than an anticoccidial vaccine administered alone. Both dose levels of *P. acnes* were better at controlling coccidiosis infections and deaths due to coccidiosis than the higher level of 16.0 μg of *P. acnes*.

EXAMPLE 17

The procedure from Example 16, above, was substantially repeated in order to determine an optimum dosage or range thereof of *P. acnes* for in ovo injection. The treatment groups were as follows in Table 13:

TABLE 10

Intestinal Lesion Scores

| Group | P. acnes | Vaccine | Challenge | Ave. Score | Upper Score | Mid Score | Cecal Score |
|---|---|---|---|---|---|---|---|
| 1 | 0.0 μg | No | No | 0.0$^d$ | 0.0$^d$ | 0.0$^d$ | 0.0$^d$ |
| 2 | 0.0 μg | No | Yes | 2.4$^a$ | 2.8$^a$ | 1.5$^a$ | 3.1$^a$ |
| 3 | 0.0 μg | Yes | No | 0.0$^d$ | 0.0$^d$ | 0.0$^d$ | 0.0$^d$ |
| 4 | 0.0 μg | Yes | Yes | 1.9$^b$ | 2.2$^b$ | 1.3$^{b,c}$ | 2.5$^b$ |
| 5 | 4.0 μg | Yes | Yes | 1.7$^c$ | 2.0$^{b,c}$ | 1.1$^c$ | 2.1$^{b,c}$ |
| 6 | 8.0 μg | Yes | Yes | 1.6$^c$ | 1.7$^c$ | 1.2$^{b,c}$ | 2.0$^c$ |
| 7 | 16.0 μg | Yes | Yes | 1.9$^b$ | 2.1$^b$ | 1.3$^{b,c}$ | 2.4$^b$ |

The number of coccidiosis deaths six days post coccidial challenge are presented in Table 11.

TABLE 11

| Group | Treatment | Number of Deaths (%) |
|---|---|---|
| 1 | 0.0 μg P. acnes, no vaccine, no challenge | 0 (0) |
| 2 | 0.0 μg P. acnes, no vaccine, challenged | 6 (10) |
| 3 | 0.0 μg P. acnes, vaccinated, no challenge | 0 (0) |
| 4 | 0.0 μg P. acnes, vaccinated, challenged | 1 (2) |
| 5 | 4.0 μg P. acnes, vaccinated, challenged | 2 (3) |
| 6 | 8.0 μg P. acnes, vaccinated, challenged | 0 (0) |
| 7 | 16.0 μg P. acnes, vaccinated, challenged | 5 (8) |

TABLE 13

| Group | P. acnes dose per egg | Anticoccidial Vaccine | Coccidiosis Challenge | Number of Embryos | Number of Chicks |
|---|---|---|---|---|---|
| 1 | 0 | No | No | 100 | 60 |
| 2 | 0 | No | Yes | 100 | 60 |
| 3 | 0 | Yes | Yes | 100 | 60 |
| 4 | 4.0 µg | No | Yes | 100 | 60 |
| 5 | 8.0 µg | No | Yes | 100 | 60 |
| 6 | 4.0 µg | Yes | Yes | 100 | 60 |
| 7 | 8.0 µg | Yes | Yes | 100 | 60 |

The purpose of this study was to determine whether 4.0 or 8.0 µg of P. acnes was the optimal dose, in ovo, for the stimulation of immunity as an aid in preventing coccidiosis in broiler chickens. 8.0 µg of P. acnes appeared to be the preferred dose over all parameters. The groups given P. acnes with a vaccine did better in all cases than the vaccine alone for all parameters.

EXAMPLE 18

The procedure from Example 16 is repeated with the exception that in ovo inoculation occurs at day 14 of incubation. Non-specific cell-mediated immune response occurs with a resulting decrease in the effects of coccidiosis on the chicks.

EXAMPLE 19

The procedure from Example 16 is repeated with the exception that in ovo inoculation occurs at day 20 of incubation. Non-specific cell-mediated immune response occurs with a resulting decrease in the effects of coccidiosis on the chicks.

The present invention may be embodied in other specific forms without departing from its spirit or essential characteristics. The described embodiments are to be considered in all respects only as illustrative and not restrictive. The present invention is not limited to stimulating an immune response against coccidiosis. To the contrary, the present invention is directed to stimulating non-specific cell mediated immunity against diseases caused by bacteria, viruses, or parasites. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for inoculating poultry against coccidiosis, comprising the steps of:
   (a) obtaining a solution comprising *Propionibacterium acnes* suspended in a diluent; and
   (b) administering an effective amount of said solution to said poultry via in ovo inoculation in order to stimulate a non-specific cell-mediated immune response.

2. The method as recited in claim 1, further comprising the step of vaccinating said poultry with an anticoccidial vaccine.

3. The method as recited in claim 2, wherein said anticoccidial vaccine is administered to said poultry simultaneously with the administration of said *Propionibacterium acnes* solution.

4. The method as recited in claim 2, wherein said anticoccidial vaccine is administered to said poultry following the administration of said *Propionibacterium acnes* solution.

5. The method as recited in claim 4, wherein said anticoccidial vaccine is administered to said poultry at the age of about day one.

6. The method as recited in claim 1, wherein said *Propionibacterium acnes* solution is administered to said poultry in ovo at least once during a period of time from about day 14 to immediately prior to hatching.

7. The method as recited in claim 1, wherein said *Propionibacterium acnes* solution is administered to said poultry in ovo at least once during a period of time from about day 17 to about day 19.

8. The method as recited in claim 1, wherein said *Propionibacterium acnes* solution is administered to said poultry in ovo at least once during day 18 in development.

9. The method as recited in claim 1, wherein said diluent comprises a normal saline solution.

10. The method as recited in claim 1, wherein said diluent comprises an amino acid solution.

11. The method as recited in claim 1, wherein said effective amount of said solution comprises a dose of *Propionibacterium acnes* in diluent of about 2 µg/egg to about 2 µg/egg.

12. The method as recited in claim 1, wherein said effective amount of said solution comprises a dose of *Propionibacterium acnes* in diluent of about 6 µg/egg to about 10 µg/egg.

13. The method as recited in claim 1, wherein said effective amount of said solution comprises a dose of *Propionibacterium acnes* in diluent of about 8 µg/egg.

14. A method for inoculating poultry against coccidiosis, comprising the steps of:
   (a) obtaining a solution comprising *Propionibacterium acnes* suspended in a diluent; and
   (b) administering an effective amount of said solution via intraperitoneal injection to said poultry following the hatching thereof in order to stimulate a non-specific cell-mediated immune response.

15. The method as recited in claim 14, further comprising the step of vaccinating said poultry with an anticoccidial vaccine.

16. The method as recited in claim 15, wherein said anticoccidial vaccine is administered to said poultry simultaneously with the administration of said *Propionibacterium acnes* solution.

17. The method as recited in claim 15, wherein said anticoccidial vaccine is administered to said poultry following the administration of said *Propionibacterium acnes* solution.

18. The method as recited in claim 17, wherein said anticoccidial vaccine is administered to said poultry at the age of about day three.

19. The method as recited in claim 14, wherein said *Propionibacterium acnes* solution is administered to said poultry at least once during a period of time immediately following the hatching of said poultry to the age of about day seven.

20. The method as recited in claim 14, wherein said *Propionibacterium acnes* solution is administered to said poultry at least once during a period of time when said poultry is younger than about three days old.

21. The method as recited in claim 14, wherein said *Propionibacterium acnes* solution is administered to said poultry at least once during a period of time when said poultry is about one day old.

22. The method as recited in claim 14, wherein said diluent comprises a normal saline solution.

23. The method as recited in claim 14, wherein said diluent comprises an amino acid solution.

24. The method as recited in claim 14, wherein said effective amount of said solution comprises a dose of *Propionibacterium acnes* in diluent of about 0.5 µg/chick to about 16 µg/chick.

25. The method as recited in claim 14, wherein said effective amount of said solution comprises a dose of *Propionibacterium acnes* in diluent of about 1.5 µg/chick to about 3.5 µg/chick.

26. The method as recited in claim 14, wherein said effective amount of said solution comprises a dose of *Propionibacterium acnes* in diluent of about 2 µg/chick.

27. A method for inoculating poultry against coccidiosis, comprising the steps of:

(a) obtaining a solution comprising *Propionibacterium acnes* suspended in a diluent; and (b) administering an effective amount of said solution via subcutaneous injection to said poultry following the hatching thereof in order to stimulate a non-specific cell-mediated immune response.

28. The method as recited in claim 27, further comprising the step of vaccinating said poultry with an anticoccidial vaccine.

29. The method as recited in claim 28, wherein said anticoccidial vaccine is administered to said poultry simultaneously with the administration of said *Propionibacterium acnes* solution.

30. The method as recited in claim 28, wherein said anticoccidial vaccine is administered to said poultry following the administration of said *Propionibacterium acne,* solution.

31. The method as recited in claim 30, wherein said anticoccidial vaccine is administered to said poultry at the age of about day three.

32. The method as recited in claim 27, wherein said *Propionibacterium acnes* solution is administered to said poultry at least once during a period of time immediately following the hatching of said poultry to the age of about day seven.

33. The method as recited in claim 27, wherein said *Propionibacterium acnes* solution is administered to said poultry at least once during a period of time when said poultry is younger than about three days old.

34. The method as recited in claim 27, wherein said *Propionibacterium acnes* solution is administered to said poultry at least once during a period of time when said poultry is about one day old.

35. The method as recited in claim 27, wherein said diluent comprises a normal saline solution.

36. The method as recited in claim 27, wherein said diluent comprises an amino acid solution.

37. The method as recited in claim 27, wherein said effective amount of said solution comprises a dose of *Propionibacterium acnes* in diluent of about 0.5 µg/chick to about 16 µg/chick.

38. The method as recited in claim 27, wherein said effective amount of said solution comprises a dose of *Propionibacterium acnes* in diluent of about 1.5 µg/chick to about 3.5 µg/chick.

39. The method as recited in claim 27, wherein said effective amount of said solution comprises a dose of *Propionibacterium acnes* in diluent of about 2 µg/chick.

40. A method for inoculating poultry against coccidiosis, comprising the steps of:

(a) obtaining a solution comprising *Propionibacterium acnes* suspended in a diluent; and (b) administering an effective amount of said solution via an eye spray to said poultry following the hatching thereof in order to stimulate a non-specific cell-mediated immune response.

41. The method as recited in claim 40, further comprising the step of vaccinating said poultry with an anticoccidial vaccine.

42. The method as recited in claim 41, wherein said anticoccidial vaccine is administered to said poultry at approximately the same time as the administration of said *Propionibacterium acnes* solution.

43. The method as recited in claim 41, wherein said anticoccidial vaccine is administered to said poultry following the administration of said *Propionibacterium acnes* solution.

44. The method as recited in claim 43, wherein said anticoccidial vaccine is administered to said poultry at the age of about three weeks.

45. The method as recited in claim 40, wherein said *Propionibacterium acnes* solution is administered to said poultry at least once during a period of time immediately following the hatching of said poultry to the age of about four weeks.

46. The method as recited in claim 40, wherein said *Propionibacterium acnes* solution is administered to said poultry at least once during a period of time when said poultry is younger than about three weeks old.

47. The method as recited in claim 40, wherein said *Propionibacterium acnes* solution is administered to said poultry at least once during a period of time when said poultry is about one day old.

48. The method as recited in claim 40, wherein said diluent comprises a normal saline solution.

49. The method as recited in claim 40, wherein said diluent comprises an amino acid solution.

50. The method as recited in claim 40, wherein said effective amount of said solution comprises a dose of *Propionibacterium acnes* in diluent of about 2 µg/chick to about 16 µg/chick.

51. The method as recited in claim 40, wherein said effective amount of said solution comprises a dose of *Propionibacterium acnes* in diluent of about 6 µg/chick to about 10 µg/chick.

52. The method as recited in claim 40, wherein said effective amount of said solution comprises a dose of *Propionibacterium acnes* in diluent of about 8 µg/chick.

* * * * *

UNITED STATES PATENT AND TRADEMARK OFFICE
CERTIFICATE OF CORRECTION

PATENT NO. : 6,019,985                              Page 1 of 2
DATED      : Feb. 1, 2000
INVENTOR(S): Jenaay M. Brown; Larry R. McDougald It is certified that error appears in the above-identified patent and that said Letters Patent is hereby corrected as shown below:

Cover Page, Other Publications, left column, line 14, change "adjuvant" to --Adjuvant--

Col. 1, line 19, change "Eimeria" to --*Eimeria*--

Col. 1, line 26, change "Eimeria" to --*Eimeria*--

Col. 2, line 58, after "with" change "ahead" to --a head--

Col. 7, line 10, after "by" delete "12"

Col. 7, line 48, change "(Gl.M)" to --(GLM)--

Col. 9, line 5, change "227 8$^b$" to --227.8$^b$--

Col. 9, line 11, change "*P. acres*" to --*P. acnes*--

Col. 9, line 63, change "*P. acres*" to --*P. acnes*--

Col. 12, line 11, change "218,6$^b$" to --218.6$^b$--

Col. 14, line 30, after "about" change "2" to --12--

UNITED STATES PATENT AND TRADEMARK OFFICE
CERTIFICATE OF CORRECTION

PATENT NO. : 6,019,985
DATED : Feb. 1, 2000
INVENTOR(S) : Jenaay M. Brown, Larry R. McDougald It is certified that error appears in the above-indentified patent and that said Letters Patent is hereby corrected as shown below:

Col. 15, line 36, change "acne" to --acnes--.

Signed and Sealed this

Twenty-seventh Day of March, 2001

Attest:

NICHOLAS P. GODICI

Attesting Officer

Acting Director of the United States Patent and Trademark Office